(12) United States Patent
Papac et al.

(10) Patent No.: US 9,192,515 B2
(45) Date of Patent: Nov. 24, 2015

(54) PNEUMATICALLY DRIVEN OPHTHALMIC SCANNING ENDOPROBE

(75) Inventors: Michael James Papac, North Tustin, CA (US); Michael J. Yadlowsky, Sunnyvale, CA (US); John Christopher Huculak, Mission Viejo, CA (US)

(73) Assignee: ALCON RESEARCH, LTD., Fort Worth, TX (US)

( * ) Notice: Subject to any disclaimer, the term of this patent is extended or adjusted under 35 U.S.C. 154(b) by 681 days.

(21) Appl. No.: 13/425,958

(22) Filed: Mar. 21, 2012

(65) Prior Publication Data

US 2012/0245569 A1 Sep. 27, 2012

Related U.S. Application Data

(60) Provisional application No. 61/466,364, filed on Mar. 22, 2011.

(51) Int. Cl.
*A61B 17/00* (2006.01)
*A61F 9/007* (2006.01)
(Continued)

(52) U.S. Cl.
CPC .......... *A61F 9/00763* (2013.01); *A61F 9/00802* (2013.01); *A61B 1/00172* (2013.01); *A61B 5/0066* (2013.01); *A61B 2017/00539* (2013.01);
(Continued)

(58) Field of Classification Search
CPC ........ A61B 17/00; A61B 10/00; A61B 18/18; A61B 17/32; A61F 9/00
USPC .............. 606/184, 4, 107, 170; 600/114, 152, 600/567; 604/22, 31
See application file for complete search history.

(56) References Cited

U.S. PATENT DOCUMENTS 3,752,161 A * 8/1973 Bent ............................. 606/184
3,976,077 A    8/1976 Kerfoot, Jr.
(Continued)

FOREIGN PATENT DOCUMENTS

DE 10 2008 036420 11/2010
GB    2222953    3/1990
(Continued)

OTHER PUBLICATIONS

Annex to Form PCT/ISAS/206 Communication Relating to the Results of the Partial International Search for corresponding PCT-US2012-029909 dated Jul. 20, 2012.
(Continued)

*Primary Examiner* — William Thomson
*Assistant Examiner* — Victor Shapiro
(74) *Attorney, Agent, or Firm* — Jason Finch

(57) ABSTRACT

An ophthalmic endoprobe including a hand-piece and a cannula assembly having a longitudinal axis is provided. The cannula assembly including an inner tube concentric with an outer tube; wherein the hand-piece may further include a motor powered by a pneumatic energy source, the motor providing motion to a transmission shaft; and a transmission system to couple the shaft motion to the cannula assembly; wherein the transmission system provides a counter-rotating motion to the inner tube and the outer tube about the longitudinal axis of the cannula. A fluid console for use in endoscopic ophthalmic microsurgery including a pneumatics module to obtain a pneumatic force from an external source and provide an adjustable pneumatic force; a scanning module coupled to the pneumatics module; and an endoprobe coupled to the scanning module is also provided.

10 Claims, 13 Drawing Sheets

(51) Int. Cl.
*A61F 9/008* (2006.01)
*A61B 1/00* (2006.01)
*A61B 5/00* (2006.01)
*A61B 17/32* (2006.01)

(52) U.S. Cl.
CPC .............. *A61B 2017/00544* (2013.01); *A61B 2017/320028* (2013.01)

(56) References Cited

U.S. PATENT DOCUMENTS

| | | | |
|---|---|---|---|
| 4,246,902 A * | 1/1981 | Martinez | 604/22 |
| 4,306,570 A * | 12/1981 | Matthews | 600/567 |
| 4,706,669 A * | 11/1987 | Schlegel | 606/107 |
| 4,865,029 A * | 9/1989 | Pankratov et al. | 606/4 |
| 4,909,249 A * | 3/1990 | Akkas et al. | 606/107 |
| 5,595,565 A | 1/1997 | Treat et al. | |
| 5,792,166 A * | 8/1998 | Gordon et al. | 606/170 |
| 6,358,199 B1 * | 3/2002 | Pauker et al. | 600/114 |
| 6,485,413 B1 | 11/2002 | Boppart et al. | |
| 7,083,591 B2 * | 8/2006 | Cionni | 604/31 |
| 7,261,687 B2 | 8/2007 | Yang | |
| 7,364,543 B2 | 4/2008 | Yang et al. | |
| 7,602,540 B2 | 10/2009 | Masuda et al. | |
| 2005/0165436 A1 | 7/2005 | Ichikawa et al. | |
| 2006/0004397 A1 | 1/2006 | Osawa | |
| 2006/0089535 A1 * | 4/2006 | Raz et al. | 600/152 |
| 2008/0228404 A1 | 9/2008 | Garty et al. | |
| 2009/0018468 A1 | 1/2009 | Janssens | |
| 2009/0198125 A1 | 8/2009 | Nakabayashi et al. | |
| 2010/0228132 A1 | 9/2010 | Brennan et al. | |
| 2011/0184390 A1 | 7/2011 | Zanni et al. | |
| 2013/0267776 A1 | 10/2013 | Brennan et al. | |

FOREIGN PATENT DOCUMENTS

| | | |
|---|---|---|
| JP | 2005185427 | 7/2005 |
| WO | 2007/038682 | 4/2007 |
| WO | 2008/079526 | 7/2008 |

OTHER PUBLICATIONS

Tearney GJ et al., "Scanning single-mode fiber optic catheter-endoscope for optical coherence tomography", Optics Letters, Apr. 1, 1996, vol. 21(7), pp. 543-545.

Han et al., "Handheld forward-imaging needle endoscope for ophthalmic optical coherence tomography inspection", Journal of Biomedical Optics, Mar./Apr. 2008, vol. 13(2), pp. 020505-1 thru 020505-3.

Wu et al., "Paired-angle-rotation scanning optical coherence tomography forward-imaging probe", Optics Letters, May 2006, vol. 31(9), 1265-1267.

Yaqoob et al., "Methods and application areas of endoscopic optical coherence tomography", Journal of Biomedical Optics, Nov./Dec. 2006, vol. 11(6), pp. 063001-1 thru 063001-19.

* cited by examiner

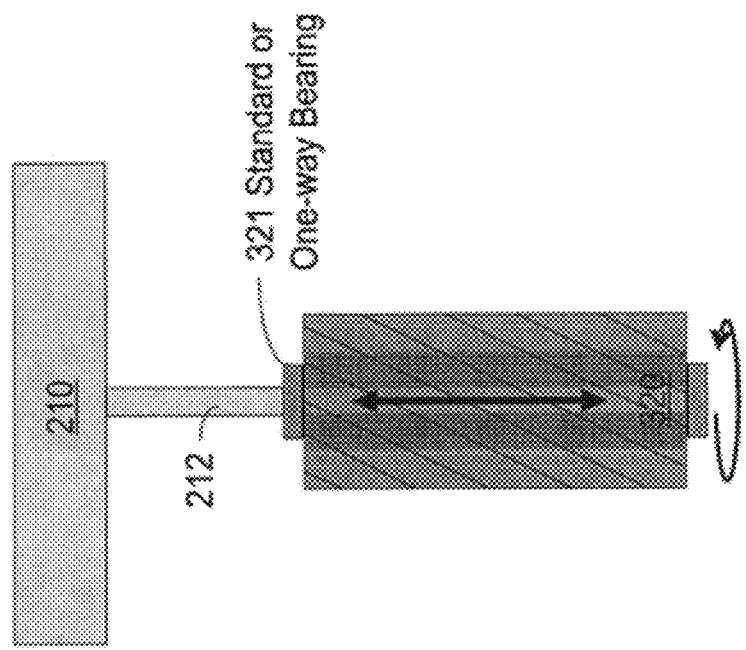

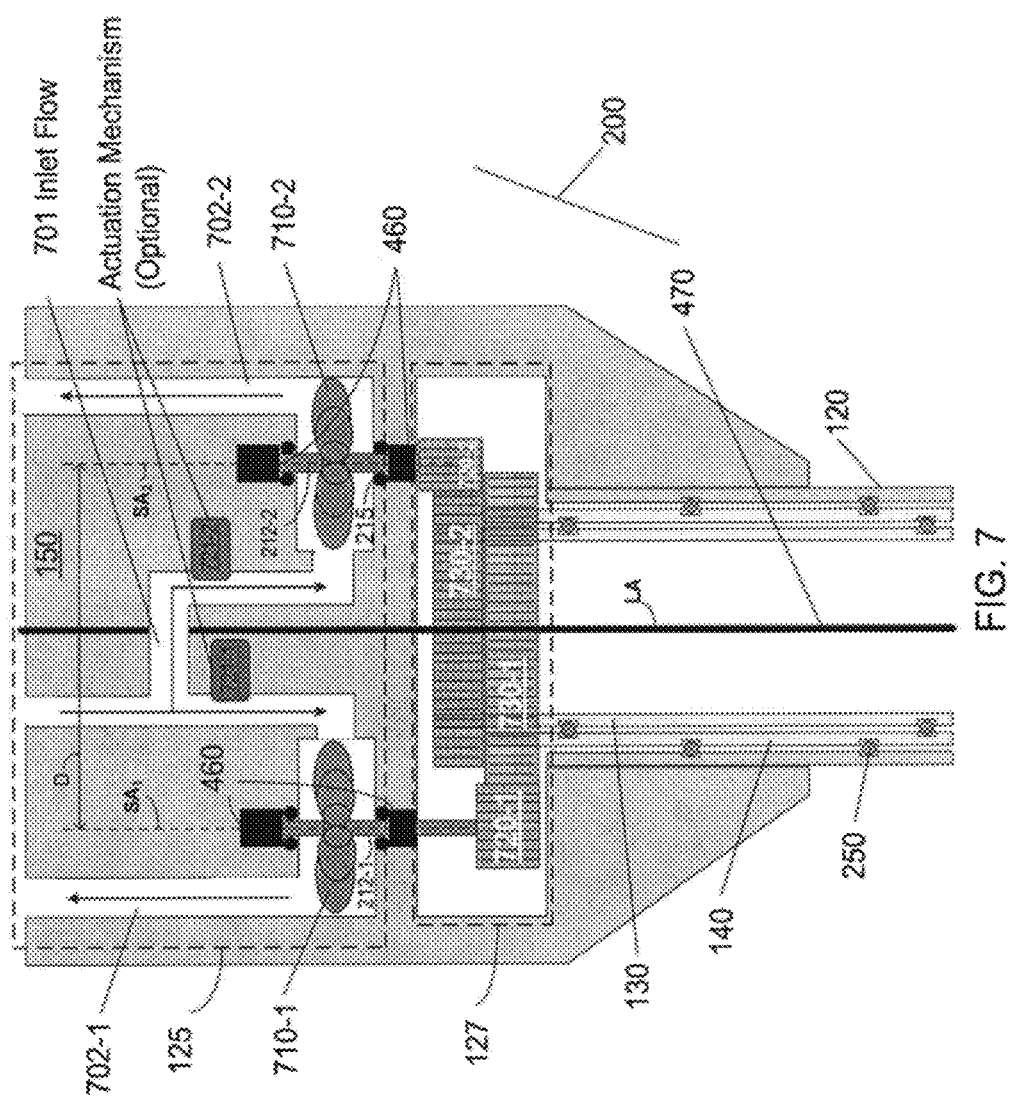

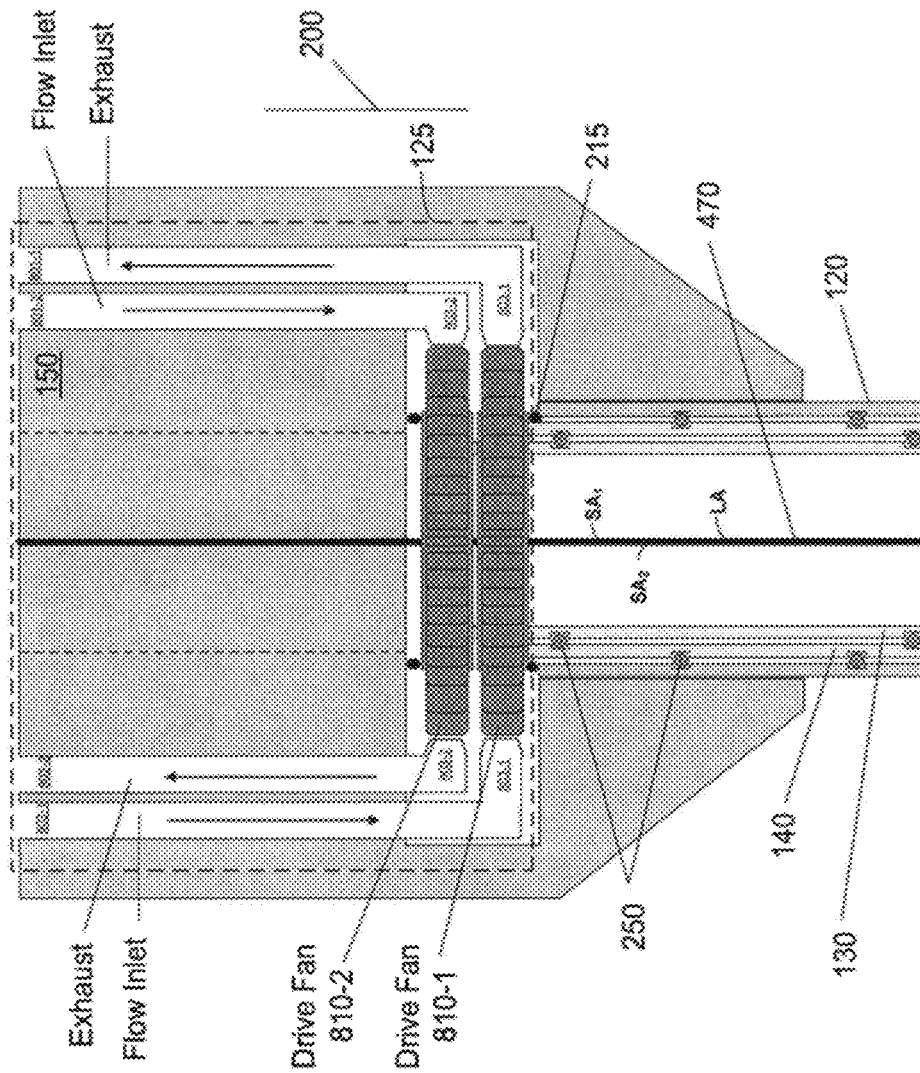

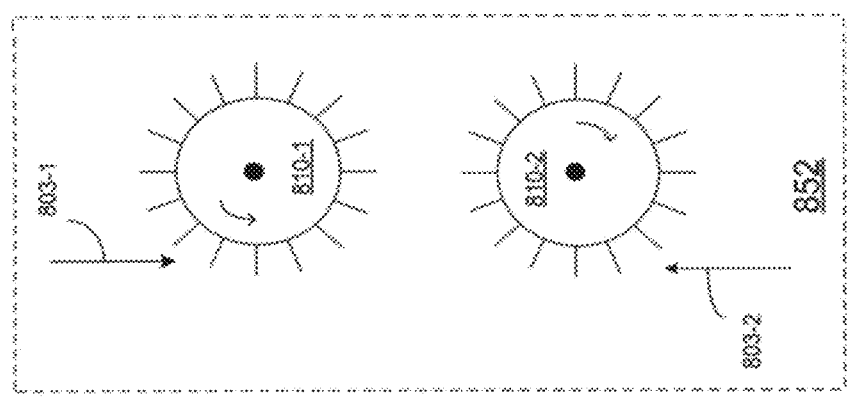
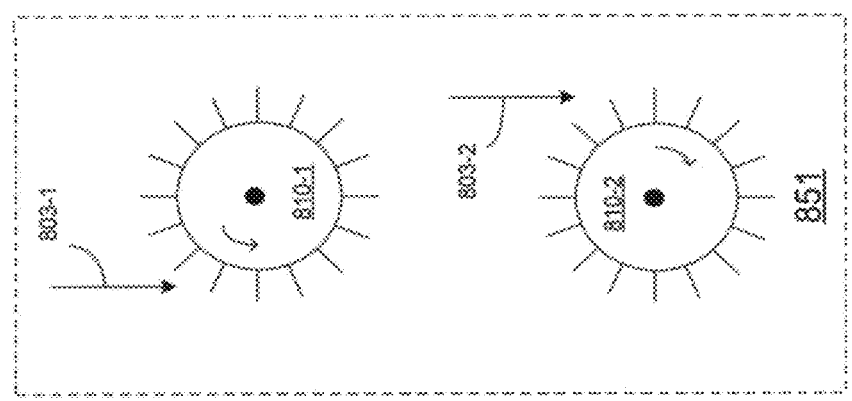
FIG. 8B

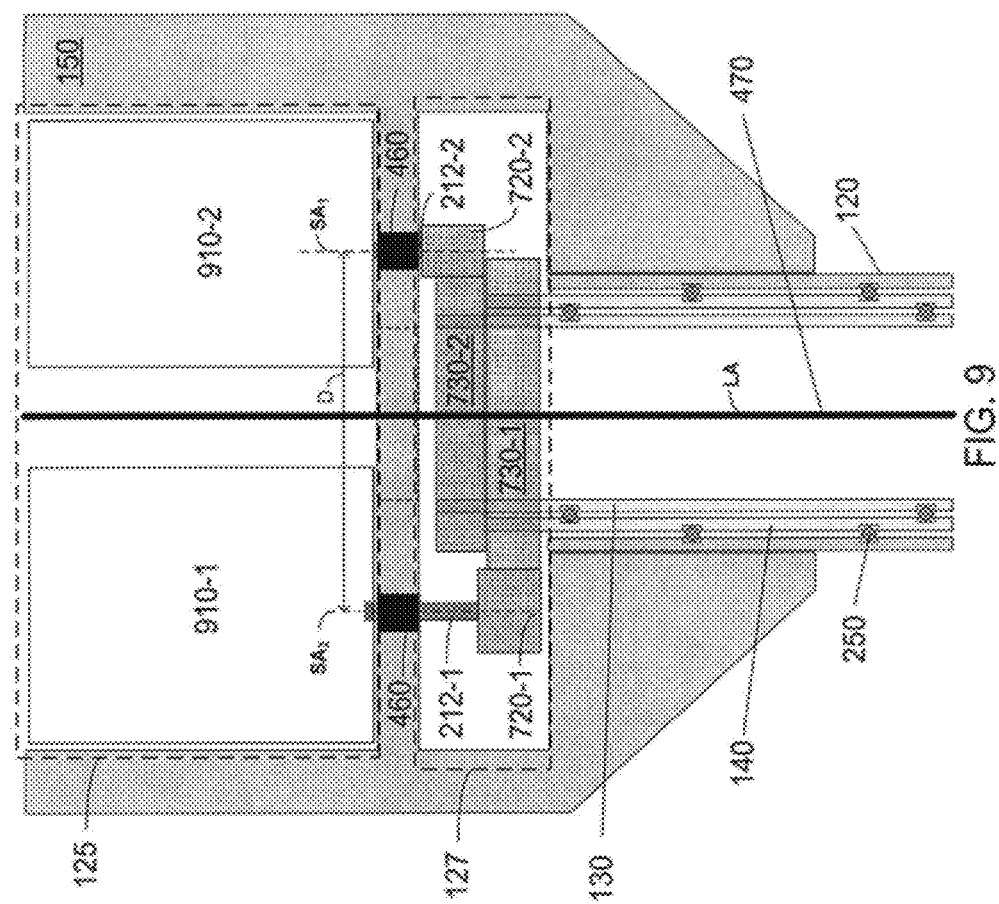

PNEUMATICALLY DRIVEN OPHTHALMIC SCANNING ENDOPROBE

CROSS-REFERENCE TO RELATED APPLICATION

This application claims priority to and benefit of U.S. provisional application Ser. No. 61/466,364 filed Mar. 22, 2011, which is herein incorporated in its entirety by reference.

BACKGROUND

1. Field of the Invention

Embodiments described herein relate to the field of ophthalmic microsurgical endoprobes. More particularly, embodiments described herein are related to the field of endoscopic Optical Coherence Tomography (OCT) and to the field of ophthalmic microsurgical techniques.

2. Description of Related Art

The field of ophthalmic microsurgical procedures is evolving rapidly. Typically, these procedures involve the use of endoprobes that are capable of reaching the tissue that is being operated or diagnosed. Such procedures make use of endoscopic surgical instruments having an endoprobe coupled to a control device in a remote console. Current state of the art provides endoprobes that are quite complex in operation, often times requiring moving parts that are operated using complex mechanical systems. In many cases, an electrical motor is included in the design of the endoprobe. Most of the prior art devices have a cost and that makes them difficult to discard after one or only a few surgical procedures. Furthermore, prior art devices generally use endoprobes having cross sections of several millimeters. These endoprobes are of little practical use for ophthalmic microsurgical techniques. In ophthalmic surgery, dimensions of one (1) millimeter or less are preferred, to cover areas typically involved without affecting unrelated tissue.

Scanning systems that allow time-dependent direction of light for diagnostic or therapeutic purposes have been used in endoscopic surgical instruments. These instruments typically use endoprobes that provide imaging, treatment, or both, over an extended area of tissue without requiring motion of the endoscope relative to its surroundings. However, efforts to develop scanning endoprobes compatible with ophthalmic surgery have been slowed by the difficulty of providing a light weight, compact drive system at a low cost. This is particularly true for forward-directed ophthalmic scanning endoprobes that may require counter rotating shafts with fixed or controlled relative speeds.

Therefore, there is a need for a simple, efficient system to provide ophthalmic microsurgical endoprobes for single-use designs. There is also a need for disposable endoprobes having light weight components that may be injection molded out of low cost materials such as plastic.

SUMMARY

A drive system for an endoprobe according to embodiments disclosed herein may include a fluid energy source; an endoprobe having a hand-piece and a cannula assembly having a longitudinal axis. The cannula assembly including an inner tube concentric with an outer tube; wherein the hand-piece may further include a motor powered by the fluid energy source, the motor providing motion to a transmission shaft; and a transmission system to couple the shaft motion to the cannula assembly; wherein the transmission system provides a counter-rotating motion to the inner tube and the outer tube about the longitudinal axis of the cannula.

Further according to embodiments disclosed herein a drive system for an endoprobe may include an electric energy source; an endoprobe having a hand-piece and a cannula assembly having a longitudinal axis. The cannula assembly including an inner tube concentric with an outer tube; wherein the hand-piece may further include a motor powered by the electric energy source, the motor providing motion to a transmission shaft; and a transmission system to couple the shaft motion to the cannula assembly; wherein the transmission system provides a counter-rotating motion to the inner tube and the outer tube about the longitudinal axis of the cannula.

According to some embodiments disclosed, a fluid console for use in endoscopic ophthalmic microsurgery may include a pneumatics module to obtain a pneumatic force from an external source and provide an adjustable pneumatic force; a scanning module coupled to the pneumatics module; and an endoprobe coupled to the scanning module.

These and other embodiments of the present invention will be described in further detail below with reference to the following drawings.

BRIEF DESCRIPTION OF THE DRAWINGS

FIG. 3B shows a piston, a transmission shaft, a rotating gear and a transmission bearing, according to some embodiments.

FIG. 7 shows a partial cross section of a portion of a hand-piece including a motor portion, a transmission system, and a cannula assembly according to some embodiments.

FIG. 8A shows a partial cross section of a portion of a hand-piece including a motor portion, and a cannula assembly according to some embodiments.

FIG. 8B shows a top-down view of a motor portion from FIG. 8A, according to some embodiments.

FIG. 9 shows a partial cross section of a portion of a hand-piece including a motor portion, a transmission system, and a cannula assembly according to some embodiments.

DETAILED DESCRIPTION

Figure 1:
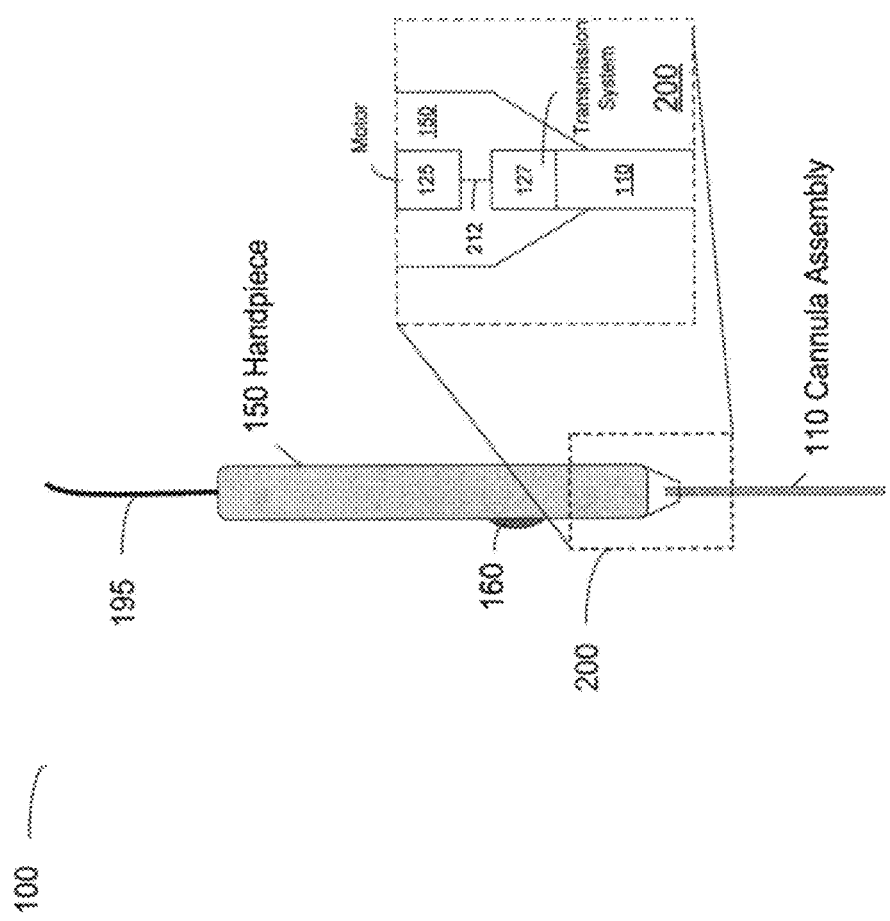
FIG. 1 shows a microsurgical endoprobe including an optical scanning element, a hand-piece, a coupling cable, and a motor portion according to some embodiments.

Microsurgical procedures using endoscopic instruments may include an endoprobe having a simple and cost-effective drive coupling system. The endoprobe may be a hand-held endoprobe for direct manipulation by specialized personnel. In some embodiments, the endoprobe may be controlled by a robotic arm or a computer-controlled device. Endoprobes have a proximal end close to the operation controller (be it a specialist or a device), and a distal end, close to or in contact with the tissue. Endoprobes according to embodiments disclosed herein may have small dimensions, be easy to manipulate from a proximal end, and be minimally invasive to the surrounding tissue. In the distal portion, the endoprobe ends with a tip, from where the endoprobe performs certain action on a target tissue located in the vicinity of the tip. For example, the endoprobe may deliver light from its tip, and receive light reflected or scattered from the tissue, coupled through the tip. The tip of the endoprobe may include movable elements that enable the tip to perform its action. In some embodiments, the tip may further include fixed elements to provide a fluid barrier and separate tissue from internal moving elements.

In some embodiments the endoprobe may include a hand-piece in the proximal end, and a cannula system in the distal end in contact with the tissue. The cannula system may be symmetric about a longitudinal axis (LA). In some embodiments, the cannula system may include an optical scanning element. The cannula system may further include two concentric cannula tubes, an inner tube and an outer tube. Further according to embodiments disclosed herein, it is desirable to provide a counter-rotating motion to the inner tube relative to the outer tube, using a single driving system. Also according to some embodiments disclosed herein, the driving system may use fluid flow, such as pneumatic flow energy. Other embodiments may use electric energy to power the driving system.

The driving system in the hand-held endoprobe may transfer pneumatic flow energy to a mechanical piston motion. Thus, the piston motion may be used to drive a gear train to counter-rotate the two cannula tubes in the distal end of the endoprobe. The piston motion is transferred to the counter-rotating cannula tubes by a transmission system. In some embodiments, the transmission system may include an oscillating gear such as a worm or spline gear. The gear may be further allowed to rotate along the piston shaft in one direction only (via one-way bearing for example) about the longitudinal axis of the cannula tubes. In some embodiments, a transmission system may include a gear system to translate a single shaft input from the piston into a coupled counter-rotating motion of the cannula tubes.

A driving system as above may further include a dual piston motor and a transmission system including uncoupled gear systems for independent drive control of each of the inner and outer tubes. In some embodiments the drive system may transfer the piston motion into a rotational motion of a shaft using a crankshaft system. If the piston motion is parallel to the cannula axis, then a gear system is used to counter-rotate the two cannulas about their individual axes. In some embodiments, the gear system may include conical gears.

In some embodiments a driving system may include constant or adjustable (non oscillatory) fluid flow to rotate a single fan connected to a shaft, coupled to a transmission system. A drive system as above may include dual fan motors to drive uncoupled gear systems for independent drive control of each of the inner and outer tubes. A drive system may include dual fan motors, each one directly coupled to a cannula tube used for independent drive control.

FIG. 1 shows microsurgical endoprobe 100 including optical scanning element 110, hand-piece 150, coupling cable 195, and motor portion 200, according to some embodiments. Optical scanning element 110 may also be referred to as a "cannula assembly" according to some embodiments. Element 110 includes the distal end of endoprobe 100 which may be elongated along the endoprobe axis and have a limited cross-section. For example, in some embodiments, cannula assembly 110 may be about 0.5 mm in diameter while hand-piece 150 may have a substantially cylindrical shape of several millimeters in diameter.

In some embodiments, assembly 110 may be in contact with tissue, including target tissue for the ophthalmic microsurgical procedure. Thus, assembly 110 may be coated with materials that prevent infection or contamination of the tissue. Furthermore, surgical procedures and protocols may establish hygienic standards for assembly 110, all of which are incorporated herein by reference in their entirety. For example, it may be desirable that assembly 110 be disposed of, after used once. In some situations, assembly 110 may be disposed of at least every time the procedure is performed on a different patient, or in a different part of the body.

Embodiments of endoprobe 100 and assembly 110 may comply with industry standards such as EN ISO 14971 (2007), "Medical Devices—Application of Risk Management to Medical Devices;" ISO/TS 20993 (2006), "Biological evaluation of medical devices—Guidance on a risk management process;" ISO 14001 (2004), "Environmental management systems—Requirements with guidance for use;" ISO 15752 (2009), "Ophthalmic instruments—endoilluminators—fundamental requirements and test methods for optical radiation safety;" and ISO 15004-2 (2007), "Ophthalmic instruments—fundamental requirements and test methods—Part 2: Light Hazard Protection." All above cited standard documents are herein incorporated by reference in their entirety.

Other embodiments of cannula assembly 110 consistent with FIG. 1 may be used. For example, embodiments such as described in U.S. patent application Ser. No. 13/354,429 filed Jan. 20, 2012 and entitled "Counter-rotating Ophthalmic Scanner Drive Mechanism" by Yadlowsky, et al., assigned to Alcon Laboratories, Inc. which is incorporated herein by reference in its entirety.

Hand-piece 150 may be closer to the proximal end of the endoprobe, and may have a larger cross section as compared to element 110. Element 150 may be adapted for manual operation of endoprobe 100, according to some embodiments. Element 150 may be adapted for robotic operation or for holding by an automated device, or a remotely operated device. While assembly 110 may be in contact with living tissue, element 150 may not be in direct contact with living tissue. Thus, even though element 150 may comply with hygienic standards, these may be somewhat relaxed as compared to those used for assembly 110. For example, element 150 may include parts and components of endoprobe 100 that may be used repeatedly before disposal.

Thus, some embodiments of endoprobe 100 as disclosed herein may include multiple components in element 150, and less expensive, replaceable components may be included in assembly 110. Some embodiments may have a removable element 110 which is disposable, while hand-piece 150 may be used more than once. In some embodiments, cannula assembly 110 may be fixed to hand-piece 150 by an adhesive bonding. According to other embodiments, assembly 110 may be removable from hand-piece 150, to allow easy replacement of endoprobe 100 for repeated procedures. Some embodiments consistent with FIG. 1 may have a disposable element 150 and a disposable assembly 110.

In some embodiments removable cannula assembly 110 may include a press in vertical insertion with separate outer screw lock. Keying may be required to maintain angular position of inner tube 130 relative to outer tube 140 during insertion of assembly 110 into hand-piece 150. Alternatively, a small adhesive tack or disposable mechanical alignment pin may be used to maintain relative angular position of inner tube 130 relative to outer tube 140 during insertion of assembly 110 into hand-piece 150. The disposable alignment pin may be removed and discarded after installation. The adhesive may be overcome by the transmission power at initial use. For fiber based probes, the fiber and support tube may be retractable. Thus, the fiber may be retracted when assembly 110 is removed and repositioned. A retractable mechanism may include a spring against a mechanical stop, or be manual. A retractable mechanism for a fiber-based endoprobe may avoid damage to the fiber in a removable assembly 110.

Cable 195 may be included in some embodiments to couple endoprobe 100 to a remote console or controller device (not shown in FIG. 1). Cable 195 may include power transmission elements, to transfer electrical or pneumatic power to a mechanical actuator or motor in motor portion 200. Cable 195 may include transmission elements to carry optical information and power, such as a laser beam or a laser pulse, from a remote console or controller to the tissue. An optical transmission element may also carry optical information from the tissue to a remote console or controller, for processing. For example, cable 195 may include at least one or more optical fibers to transmit light to and from the tissue. In some embodiments, one optical fiber may transmit light to the tissue, and another optical fiber may transmit light from the tissue. Further, some embodiments may transmit light to and from the tissue through one optical fiber.

According to some embodiments consistent with FIG. 1, endoprobe 100 is controlled through the remote console, and all operational buttons and manual actuators located remotely. Some of the control operations may include turning pneumatic power 'on' or 'off,' or adjusting the rotational speed of cannula assembly 110. Some embodiments use a Graphic User Interface (GUI) to provide controls at the console. In other embodiments, the surgeon or medical personnel may use a foot switch, or a voice command to control the operation of endoprobe 100. Some embodiments, such as illustrated in FIG. 1, include button 160 on the side, providing direct control of certain operations in endoprobe 100 by squeezing the button. Other devices used in conjunction with endoprobe 100 such as forceps or scissors may also include actuators that the surgeon can squeeze with his/her hand, to turn 'on' and 'off.'

Cable 195 may also include tubing lines (not shown in FIG. 1) to provide a pneumatic force to motor portion 200. For example, a first tubing line may include an input fluid flow providing a pneumatic force to motor portion 200. Further, a second tubing line may include an output fluid flow providing an exhaust for motor portion 200. Further according to some embodiments, a first tubing line may include an input fluid providing a first pressure to motor portion 200. A second tubing line may include an input fluid providing a second pressure to motor portion 200. In some embodiments, cable 195 may provide electrical power to motor portion 200. For example, motor portion may include at least one electric motor receiving power from cable 195.

Some embodiments consistent with FIG. 1 may include hand-piece 150 with a removable cannula assembly 110. Assembly 110 may be easily removable from hand-piece 150 by a snap-on system, or a bayonet system. Hand-piece 150 may include a bearing and a bushing coupled to the proximal end of assembly 110 to provide support and stability.

In embodiments such as shown in FIG. 1 it may be desirable that microsurgical endoprobe 100 have minimal cross sectional area. This may reduce the invasiveness of the surgical procedure on the target tissue, especially in areas adjacent to the areas of interest. In order to limit the cross sectional area of the cannula assembly in endoprobe 100, mechanical elements involved in moving parts of the endoprobe need to be placed close together.

Motor portion 200 may be included in a distal end of hand-piece 150. According to embodiments of endoprobe 100 as illustrated in FIG. 1, portion 200 may have a tapered profile in order to couple hand-piece 150 with assembly 110. For example, in some embodiments hand-piece 150 may have a larger diameter (in the order of several mm to 1 cm, or more), and assembly 110 may have a smaller diameter (from 100 μm or less to a few 100's of μm up to 0.5 mm, or more). Portion 200 may include motor 125 and transmission shaft 212 to couple motor 125 to transmission system 127. Portion 200 will be described in detail in relation to embodiments consistent with FIGS. 2-8, and FIG. 10, below.

Figure 2:
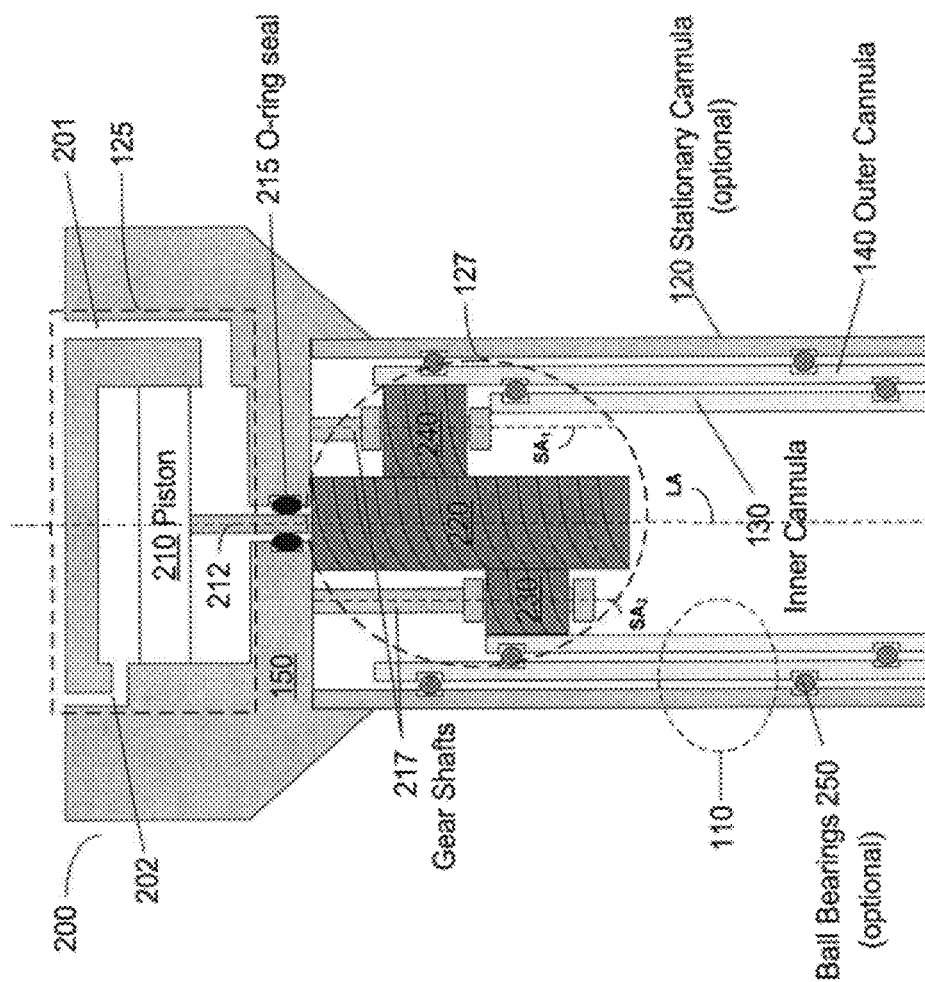
FIG. 2 shows a partial cross section of a portion of a hand-piece including a motor portion, a transmission system and a cannula assembly, according to some embodiments.

FIG. 2 shows a portion of hand-piece 150 including motor portion 200 and assembly 110, according to some embodiments. Motor 125 may include piston 210, pneumatic fluid channel 201, and pneumatic fluid channel 202. Transmission system 127 in embodiments consistent with FIG. 2 may be a helical spline including worm gears 220, 230, and 240. In some embodiments, transmission system 127 may include a spline gear in either one of gears 220, 230, and 240. Shaft 212 couples piston 210 to worm gear 220.

According to FIG. 2, pneumatic flow channel 201 provides pneumatic force to piston 210 in one direction through a first pressure. Pneumatic flow channel 202 provides pneumatic force to piston 210 in the opposite direction through a second pressure. For example, an increase in pressure in channel 201 may push piston 210 'down.' While an increase in pressure in channel 202 may push piston 210 up. The opposite configuration may also apply, namely a decrease in pressure in channel 202 pulls piston 210 'up.' Likewise, a decrease in pressure in channel 201 may pull piston 210 'down.' Also, a combination of "push" and "pull" pneumatic forces may be used in some embodiments. For example, while the pressure in channel 201 is reduced, pressure in channel 202 may be increased. Thus, a pulling force from channel 201 may be added to a pushing force in channel 202 to move piston 210 'down.' Also, a pushing force from channel 201 may be added to a pulling force in channel 202 to move piston 210 'up.' The pneumatic force provided to piston 210 through channels 201 and 202 may include a vacuum system. Thus, a vacuum may be coupled to a channel 201 (or 202) to reduce the pressure in the channel below that of the opposite channel 202 (or 201).

Motor portion 200 according to FIG. 2 may include seal 215 around shaft 212. Seal 215 may be an o-ring formed of a resilient material, such as rubber. Seal 215 may prevent the fluid inside motor 125 from coming in contact with the space inside assembly 110. Thus, seal 215 avoids contamination of the elements inside assembly 110 by the fluid for motor 125. Seal 215 also keeps the pressure level inside motor 125 at an appropriate value.

Transmission system 127 may include worm gears 220, 230 and 240 according to embodiments consistent with FIG. 2. Gears 220, 230 and 240 may have parallel axes. As illustrated in FIG. 2, the rotation axis of gear 220 is the longitudinal axis (LA) of assembly 110. Gear 230 has a rotation axis labeled $SA_2$ and gear 240 has a rotation axis labeled $SA_1$. In embodiments consistent with FIGS. 2-9, the longitudinal axis of assembly 110 is labeled LA. The axis in system 127 about which a rotating motion is provided to inner tube 130 is labeled $SA_2$ in embodiments consistent with FIGS. 2-9. The axis in system 127 about which a rotating motion is provided to outer tube 140 is labeled $SA_1$ in embodiments consistent with FIGS. 2-9. According to embodiments consistent with FIG. 2, axes $SA_1$ and $SA_2$ are parallel to axis LA. Other embodiments may have different configurations for axes $SA_1$ and $SA_2$, relative to axis LA. Further according to FIGS. 2-9, axes $SA_1$ and $SA_2$ may be parallel to each other, having a distance 'D' between them. Note that in embodiments consistent with FIG. 2 the distance between LA and $SA_1$ may not be the same as the distance between LA and $SA_2$. Some embodiments consistent with the concept illustrated in FIG. 2 may be such that axes LA, $SA_1$ and $SA_2$ may not be included in the same plane, but are included within the outer diameter of assembly 110. Other embodiments may have axes LA, $SA_1$ and $SA_2$ oriented at any angle with respect to each other. Further, some embodiments may include axes LA, $SA_1$ and $SA_2$ collinear with each other.

According to FIG. 2, gear 220 may be fixed to shaft 212 and gears 230 and 240 may be allowed to rotate about shafts 217. Gear 220 is moved 'up' and 'down' by shaft 212 when pneumatic forces move piston 210 according to the description above. As gear 220 is moved, it pushes on the grooves of gears 230 and 240. The pushing of gear 220 on gears 230 and 240 exerts a torque that induces a rotation in gears 240 and 230 about shafts 217.

FIG. 2 includes cannula assembly 110. Assembly 110 is coupled to motor 125 in hand-piece 150 through transmission system 127. Assembly 110 may include concentric tubes, or 'cannulae,' 130 and 140, according to some embodiments. Inner tube 130 and outer tube 140 may be aligned with their symmetry axes along the LA. Inner tube 130 and outer tube 140 are hollow, and may be able to move relative to each other in a rotating and counter rotating motion about the LA. The reference to inner tube 130 as "rotating" and outer tube 140 as "counter-rotating" is arbitrary and establishes the relative motion between tubes 130 and 140. In some embodiments, while tube 130 rotates 'clockwise,' tube 140 may rotate 'counter-clockwise' about axis LA. The opposite configuration may occur, wherein tube 130 rotates 'counter-clockwise' and tube 140 rotates 'clockwise.'

The rotation of tubes 130 and 140 is provided by motor 125 through gears 230 and 240, as shown in FIG. 2. Gears 230 and 240 may rotate in the same direction at any point in time, providing co-rotating cannula tubes 130 and 140. In embodiments consistent with FIG. 2 used for optical scanning (e.g. in OCT), a rotating scan pattern of an optical beam may result. In such configuration, co-rotating tubes 130 and 140 may still provide a fixed linear optical scan pattern by synchronizing the detection so that each adjacent point along a fixed line is optically captured during a different revolution of cannula assembly 110. Other embodiments of co-rotating tubes 130 and 140 consistent with FIG. 2 may be used for rotating optical line scans in volume imaging. Gears 230 and 240 are coupled to cannula tubes 130 and 140 respectively, through threaded guides on the inside wall of the cannulae or tubes.

Some embodiments consistent with FIG. 2 may include stationary cannula 120. Cannula 120 may provide a protective cover to assembly 110. Also, cannula 120 may prevent or reduce shear strain induced in the target tissue by viscoelastic forces acting upon the rotation of outer tube 140. The use of stationary cannula 120 is optional and may be determined by the type of target tissue where endoprobe 100 will be introduced.

The materials used to form cannula elements 120, 130, and 140 may be any of a variety of biocompatible materials. For example, some embodiments may include elements 120, 130 and 140 made of stainless steel, or plastic materials. Furthermore, some embodiments may have a portion or the entirety of elements 120, 130 and 140 coated with a protective layer. The coating material may be a gold layer, or some biocompatible polymer. In some embodiments the role of the coating layer may be to provide lubrication and friction relief to moving parts in assembly 110. For example, coating materials may reduce friction between the inner face of tube 140 and the outer face of tube 130. In some embodiments the role of the coating layer may be to provide protection to the tissue in direct contact with assembly 110.

To reduce friction between inner tube 130 and outer tube 140 as they counter rotate relative to each other, some embodiments of assembly 110 may include ball bearings 250. Bearings 250 may be interspaced at predetermined distances along the length of assembly 110. In embodiments including fixed cannula 120, bearings 250 may also be included between outer tube 140 and fixed cannula 120. Ball bearings 250 may be formed of a material such as stainless steel, or a hardened plastic, such as vinyl. Other materials may be used to provide friction relief to the moving parts in assembly 110, such as copper or aluminum, and polymer coatings.

Figure 3A:
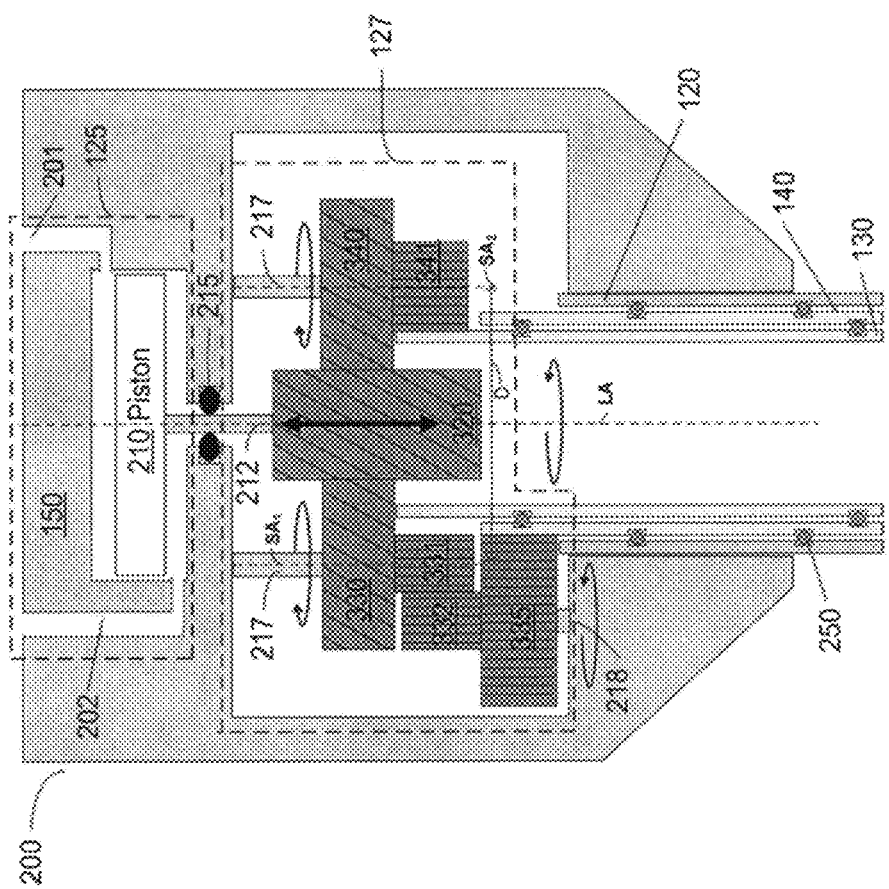
FIG. 3A shows a partial cross section of a portion of a hand-piece including a motor portion, a transmission system and a cannula assembly, according to some embodiments.

FIG. 3A shows a portion of hand-piece 150 including motor portion 200, transmission system 127 and cannula assembly 110, according to some embodiments. Motor portion 200 in FIG. 3A includes motor 125 with piston 210, shaft 212, seal 215, and pneumatic flow channels 201 and 202, as described above in relation to FIG. 2. Assembly 110 in FIG. 3A includes inner tube 130, outer tube 140, and optionally, some embodiments may include ball bearings 250 and fixed cannula 120. Assembly 110 has been described in detail in relation to FIG. 2 above.

Transmission system 127 according to FIG. 3A includes rotating worm gear 320, and gears 330, 331, 332, 335, 340, and 341. Axes LA, $SA_1$ and $SA_2$ in FIG. 3A are parallel to each other, as described in detail in relation to FIG. 2. Gear system 127 couples the 'up' and 'down' motion of shaft 212 into a counter-rotating motion between inner tube 130 and outer tube 140. In embodiments consistent with FIG. 3A, as worm gear 320 is allowed to rotate about shaft 212 in one direction, it induces a rotation of gears 330 and 340 in the opposite direction via a 'worm' coupling of the threaded faces of the gears.

Gear 341 is attached to gear 340, and provides a rotation to inner tube 341. In some embodiments consistent with FIG. 3A, gear 341 may be fixed relative to gear 340, rotating about the same axis $SA_2$. Gear 331 is attached to gear 330, and provides a rotation to gear 332 in the opposite direction. Gear 332 may be attached to gear 335, which provides a rotation to outer tube 140. In embodiments consistent with FIG. 3A, gears 330 and 331 may be fixed relative to one another, and rotate about the same axis $SA_2$. Gears 332 and 335 may also be fixed relative to one another and rotate about the same axis 218. As a result, transmission system 127 in FIG. 3A may provide a counter-rotating motion between inner tube 130 and outer tube 140. For example, while gears 330 and 340 may both rotate clockwise, inner tube 130 may be rotated counter-clockwise by gear 341. And outer tube 140 may be rotated clockwise by gear 335, which in turn is rotated counter-clockwise by gear 331. The detailed coupling between motor 125 and rotating gear 320 is described in FIG. 3B.

FIG. 3B shows piston 210, transmission shaft 212, rotating gear 320, and transmission bearing 321, according to some embodiments. Bearing 321 allows gear 320 to rotate about shaft 212 when piston 210 moves 'up' and 'down,' according to embodiments consistent with FIGS. 3A and 3B. For example, as shaft 212 is moved 'down' by piston 210, gear 320 may be rotated clockwise or counter clockwise by the reaction torque of gears 330 and 340 placed in contact with it (cf. FIG. 3A). Whether gear 320 moves clockwise or counter clockwise when piston 210 moves 'down' depends on the orientation of the 'worm' thread on the surface of gear 320. In the embodiment illustrated in FIG. 3B, the worm thread on gear 320 is such that it rotates clockwise as piston 210 moves 'down.' Some embodiments may have the opposite configuration, such that gear 320 rotates counter-clockwise when piston 210 moves 'down.'

When piston 210 moves 'up,' different embodiments may be consistent with FIG. 3B. In embodiments such that transmission bearing 321 is a standard, bidirectional bearing, then gear 320 may rotate in the opposite direction as it does when piston 210 moves 'down.' This is due to the reaction torque of gears 330 and 340 placed in contact with gear 320 (cf. FIG. 3A). In this scenario system 127 (cf. FIG. 3A) provides a counter rotating motion to inner tube 130 relative to outer tube 140 which is opposite to the counter-rotating motion when piston 210 moves 'down.' For example, when piston 210 moves 'down' inner tube 130 may rotate clockwise and outer tube 140 may rotate counter-clockwise. And when piston 210 moves 'up' inner tube 130 may rotate counter-clockwise and outer tube 140 may rotate clockwise. The result will be a 'spooling' motion of cannula assembly 110. A 'spooling' motion of assembly 110 may reduce abrasion to the tissue in direct contact with cannula assembly 110. A 'spooling' motion is such that tubes 130 and 140 rotate in one direction for one cycle, and switch to rotate in the opposite direction in the next cycle. Thus, while the scanning effect is a linear trajectory, the tissue surrounding assembly 110 is subjected to reduced shear.

In other embodiments consistent with FIG. 3B, bearing 321 may be a one-directional bearing or one-way bearing, so that it is allowed to rotate only in one direction (clockwise or counter-clockwise). Thus, as shaft 212 is moved 'up' and 'down' by piston 210 the result is that gear 320 rotates gears 330 and 340 in one direction. The rotation direction of gears 330 and 340 may be clockwise or counter clockwise depending on which direction one-directional gear 321 is allowed to rotate. For example, bearing 321 may allow gear 320 only to rotate clockwise about shaft 212. In such configuration, gears 330 and 340 will rotate counterclockwise when piston 210 moves 'up' and when piston 210 moves 'down.'

Figure 3C:
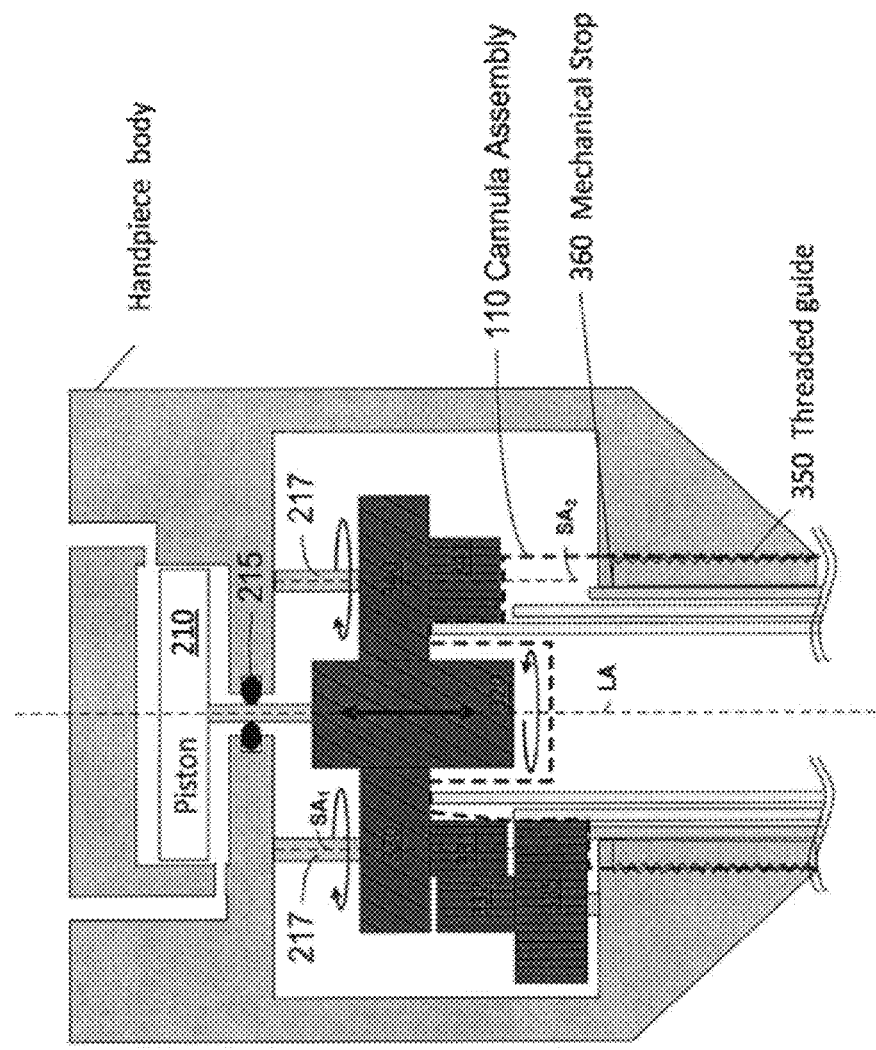
FIG. 3C shows a partial cross section of a portion of a hand-piece including a motor portion, a transmission system, and a cannula assembly attached to the hand piece using a threaded guide, according to some embodiments.

FIG. 3C shows a partial cross section of a portion of hand-piece 150 including motor portion 200, transmission system 127, and detachable cannula assembly 110, according to some embodiments. Assembly 110 is attached to hand piece 150 using threaded guide 350. Mechanical stop 360 secures assembly 110 in place. Threaded guide 350 and stop 360 ensure that proximal ends of inner tube 130 and outer tube 140 make proper contact with gears 341 and 335 of transmission system 127, respectively.

It would also be evident that other embodiments of endoprobe 100 with hand-piece 150 and detachable cannula assembly 110 may be possible. For example, instead of threaded guide 350, cannula assembly 110 may simply snap onto hand-piece 150 and stay in place by pressure. In some embodiments, a bayonet mechanism may replace threaded guide 350 with a groove and pins that secure assembly 110 in place by locking into holes or spaces carved into hand-piece 150. Other embodiments of hand-piece 150 having detachable cannula assembly 110 will be evident for those skilled in the art in view of the concept illustrated in FIG. 3C.

Figure 4:
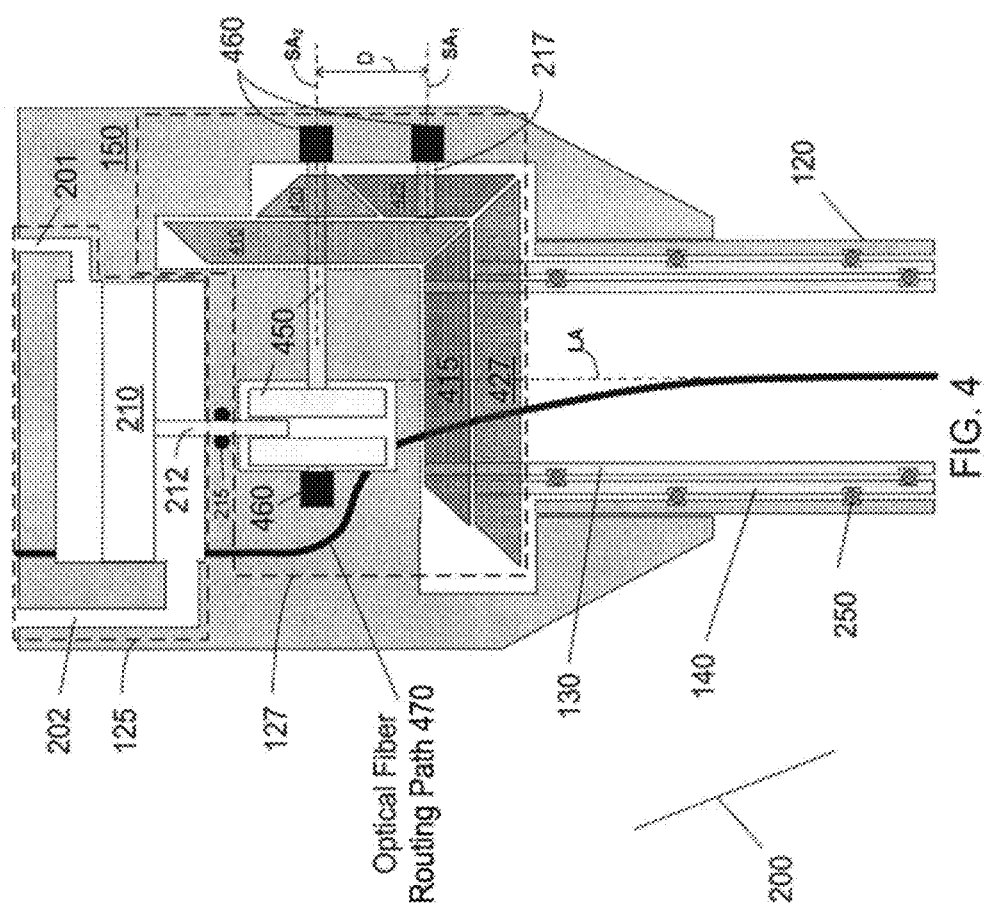
FIG. 4 shows a partial cross section of a portion of a hand-piece including a motor portion, a transmission system, and a cannula assembly according to some embodiments.

FIG. 4 shows a portion of hand-piece 150 including motor portion 200 and cannula assembly 110, according to some embodiments. Motor 125 in embodiments consistent with FIG. 4 includes piston 210, transmission shaft 212, and pneumatic flow channels 201 and 202. Also included in FIG. 4 is seal 215 as described above in relation to FIG. 2. Motor 125 operates in a manner consistent with the description provided in FIG. 2 and in FIG. 3A. Cannula assembly 110 in FIG. 4 includes inner tube 130 and outer tube 140. Some embodiments may also include ball bearings 250 and fixed cannula 120. Assembly 110 in FIG. 4 is consistent with the description of assembly 110 in FIG. 2 and in FIG. 3A above.

Transmission system 127 in motor portion 200 couples the 'up' and 'down' motion of shaft 212 to a counter-rotating motion of tubes 130 and 140 in assembly 110. According to embodiments consistent with FIG. 4, transmission system 127 may include crankshaft 450, shaft bearings (bushings) 460, conical gears 410, 415, 420, 425 and 427, and rotating axis 217. Crankshaft 450 converts the 'up' and 'down' motion of shaft 212 into a rotating motion. Crankshaft 450 hinges on portion 200 through bushings 460 in both ends. Bushings 460 allow rotation and provide support to crankshaft 450. As illustrated in FIG. 4, crankshaft 450 may be perpendicular to shaft 212. Counter-rotating tubes 130 and 140 in cannula assembly 110 have an axis parallel to shaft 212. Thus, conical gears 410, 415, 420, 425 and 427 may be used to convert the rotation of crankshaft 450 into a rotation about the axis of cannula assembly 110, as shown in FIG. 4.

According to embodiments consistent with FIG. 4, gears 410 and 420 may have an axis on crankshaft 450, and be fixed to it. Gear 415, oriented in a plane perpendicular to that of gear 410, has its axis along the axis of assembly 110. Gear 415 may be fixed to inner tube 130 in assembly 110. Thus, rotation of gear 410 with crankshaft 450 induces a rotation of inner tube 130. Likewise, gear 427 is oriented in a plane perpendicular to that of gear 420 and has its axis along the axis of assembly 110. Gear 427 may be fixed to outer tube 140, and coupled to gear 420 through gear 425. Gear 425 may be in the same plane as gear 420, with its axis on shaft 217, parallel to crankshaft 450. Shaft 217 hinges on portion 200 through bushing 460, allowing shaft 217 and gear 425 to rotate as gear 420 rotates. As gear 420 rotates, it transmits a rotation to gears 425 and 427, thus rotating outer tube 140. The inclusion of gear 425 in the transmission train from crankshaft 450 to outer tube 140 provides a counter-rotating motion relative to tube 130. Accordingly, in embodiments consistent with FIG. 4 axes $SA_1$ and $SA_2$ may be parallel to each other and may form a plane including axis LA. However, axis LA is perpendicular to axes $SA_1$ and $SA_2$. Furthermore, in some embodiments consistent with FIG. 4 axis LA may not be in the plane formed by parallel axes $SA_1$ and $SA_2$.

FIG. 4 also illustrates optical fiber routing path 470. Path 470 may be a hole bored through motor portion 200 to allow for an optical fiber to reach the distal end of assembly 110. Path 470 may also include a plurality of optical fibers, such as an optical fiber bundle. Path 470 may be formed by drilling a hole through portion 200. In some embodiments, path 470 may be formed by joining two molded halves of portion 200, each having a groove or channel molded in, for path 470.

Figure 5:
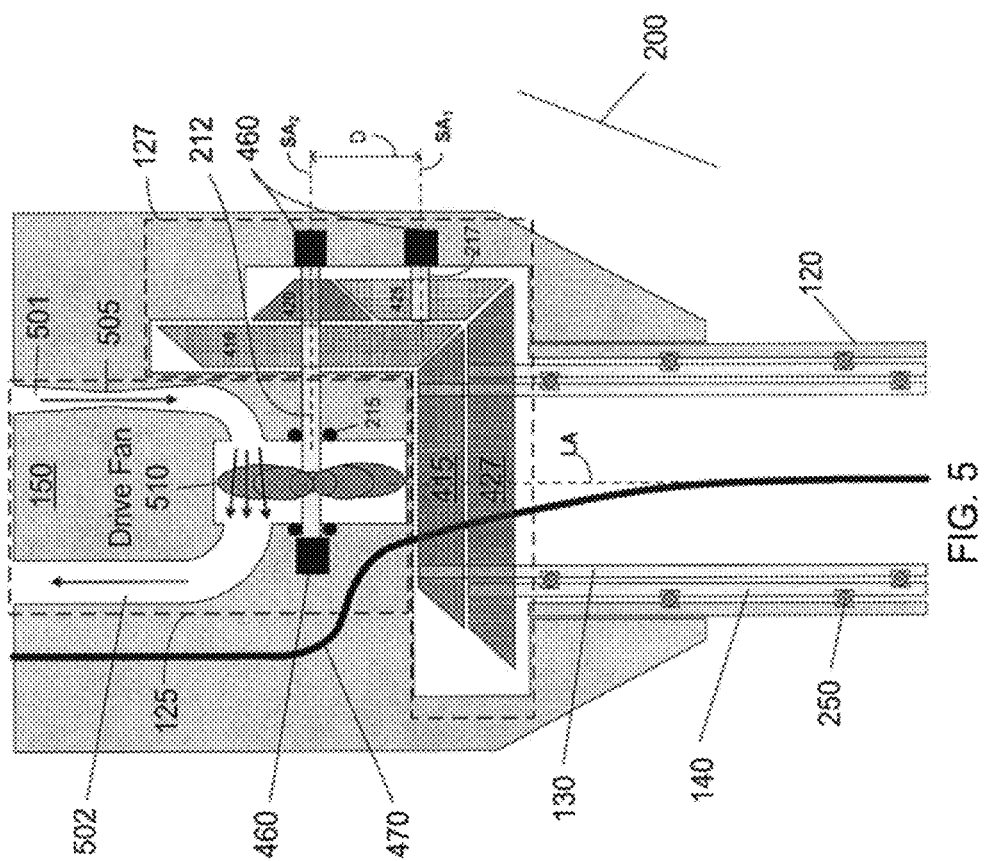
FIG. 5 shows a partial cross section of a portion of a hand-piece including a motor portion, a transmission system, and a cannula assembly according to some embodiments.

FIG. 5 shows a portion of hand-piece 150 including motor portion 200 and cannula assembly 110, according to some embodiments. Motor 125 in FIG. 5 may include input flow channel 501, speed adjuster 505, drive fan 510, and exhaust tube 502. Also included in FIG. 5 is seal 215 as described above in relation to FIG. 2. According to embodiments consistent with FIG. 5 fluid flows continuously from input flow channel 501 to exhaust tube 502. Speed adjuster 505 may increase or decrease the flow speed through fan 510. Transmission system 127 in embodiments consistent with FIG. 5 is analogous to system 127 described with relation to FIG. 4. Thus, the arrangement of axes $SA_1$ and $SA_2$ relative to axis LA in FIG. 5 follows the description of that in FIG. 4.

According to embodiments consistent with FIG. 5, a fluid flows continuously from channel 501 to channel 502. As the fluid impinges on fan 510, it provides a rotating motion to shaft 212 about its axis. In some embodiments, fan 510 includes blades spanning a surface area perpendicular to a plane including the axis of shaft 212. Furthermore, the blades may be bent so that each blade spans a portion of a helicoid about shaft 212. The helicoid is oriented in the same direction for all blades: clockwise or counter-clockwise. The specific orientation of the helicoid and the direction of the fluid flow may determine the direction of rotation of shaft 212. As illustrated in FIG. 5, motor 125 may include speed adjuster 505 in channel 501. Speed adjuster 505 is placed 'upstream' from fan 510. In embodiments consistent with FIG. 5 adjuster 505 may provide a constriction in channel 501 so as to create a Venturi effect to the flow. In such configuration, a Venturi effect for an incompressible or almost incompressible fluid includes a reduction in the flow cross-section and an increase in the speed of the flow. Thus, the momentum transfer from the fluid to the rotational motion of shaft 212 may be increased. The degree of speed increase may be changed by adjusting precisely the cross section of channel 501. Thus, some embodiments consistent with FIG. 5 may provide a speed control for the rotational motion of tubes 130 and 140 in assembly 110.

Assembly 110 in FIG. 5 is consistent with the description of assembly 110 in FIG. 2 and in FIG. 3A above. Also, fiber routing path 470 in FIG. 5 is consistent with the description provided in relation to FIG. 4, above.

Figure 6:
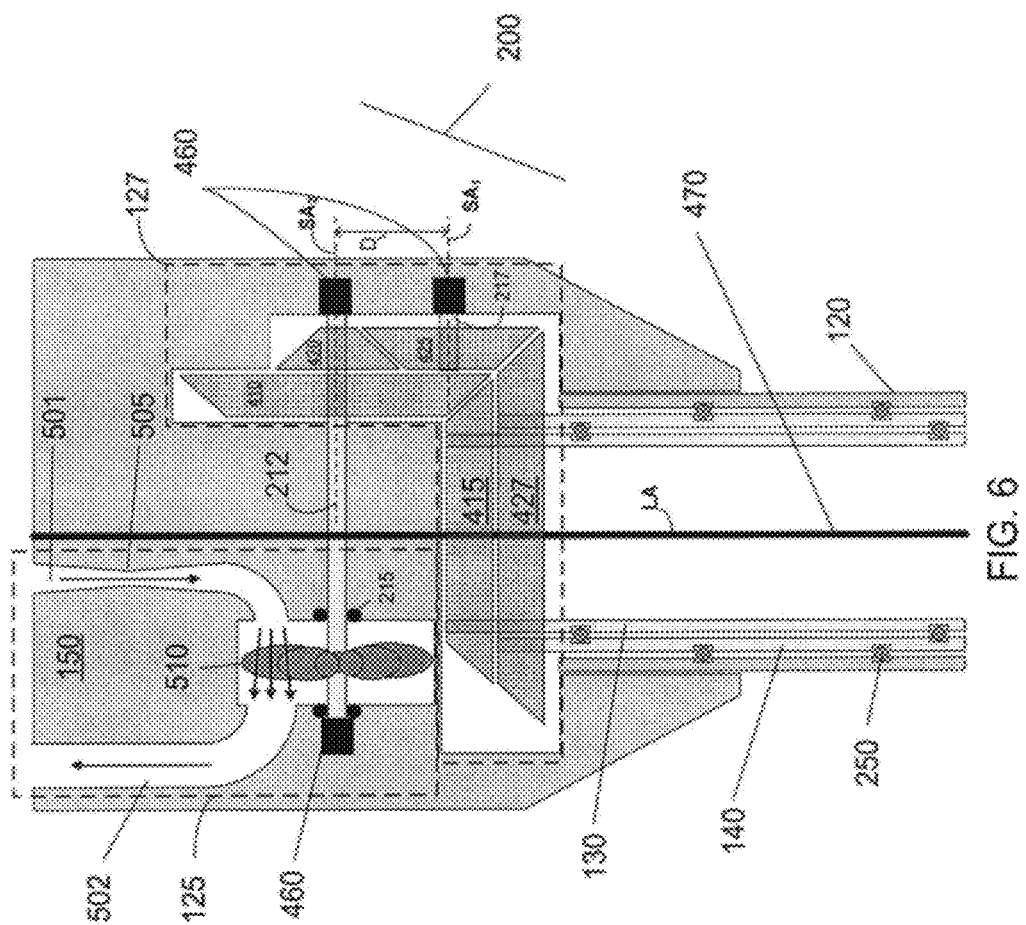
FIG. 6 shows a partial cross section of a portion of a hand-piece including a motor portion, a transmission system, and a cannula assembly according to some embodiments.

FIG. 6 shows a portion of hand-piece 150 including motor portion 125, transmission system 127, and cannula assembly 110, according to some embodiments. Motor portion 125 in FIG. 6 is consistent with the description provided above in relation to FIG. 5. Transmission system 127 is consistent with the description provided above in relation to FIG. 4. Thus, while axes $SA_1$ and $SA_2$ are parallel to each other, axis LA is perpendicular to both. Assembly 110 in FIG. 6 is consistent with the description of assembly 110 in FIG. 2 and in FIG. 3A above. Also included in FIG. 6 is seal 215 as described above in relation to FIG. 2. According to embodiments consistent with FIG. 6, fiber routing path 470 may run along axis LA. Thus, bending of optical fibers and other elements included in path 470 is reduced to a minimum. In order to provide path 470 as illustrated in FIG. 6, motor 125 may be placed to the side of hand-piece 150, increasing the length of shaft 212.

FIG. 7 shows a portion of hand-piece 150 including motor portion 125, transmission system 127, and cannula assembly 110, according to some embodiments. Motor portion 125 may include two motors, each motor including a fan 710-1 and 710-2 as in FIGS. 5 and 6, and placed on either side of hand-piece 150, around fiber path 470. In FIG. 7 fiber path 470 is as described in relation to FIG. 6. Also included in FIG. 7 are seals 215 as described above in relation to FIG. 2. Assembly 110 in FIG. 7 is consistent with the description of assembly 110 in FIG. 2 and in FIG. 3A above.

According to embodiments consistent with FIG. 7, motor 125 may include inlet flow path 701 feeding both fans 710-1 and 710-2. The exhaust flow may leave engine 125 through two channels 702-1 and 702-2, after impinging on each fan 710-1 and 710-2, respectively. Additionally, some embodiments may include actuators 721-1 and 721-2 providing a speed adjustment control as described in relation to adjuster 505 in FIG. 5. Thus, embodiments consistent with FIG. 7 may provide a separate adjustment to the speed of fans 710-1 and 710-2. In some embodiments, the blades in fans 710-1 and 710-2 may be oriented in opposite directions, so that shafts 212-1 and 212-2 rotate and counter-rotate relative to each other. This system takes advantage of a single pneumatic force providing rotational motion in two opposing directions and simplifying the design of transmission system 127.

Transmission system 127 as illustrated in FIG. 7 may include gears 720-1 and 730-1 coupling the rotation of shaft 212-1 to outer tube 140. System 127 may also include gears 720-2 and 730-2 coupling the rotation of shaft 212-2 to inner tube 130. Other configurations consistent with FIG. 7 may be possible, for example gears 720-2 and 730-2 coupling the rotation of shaft 212-2 to outer tube 140 and gears 720-1 and 730-1 coupling the rotation of shaft 212-1 to inner tube 130. In such configuration, a rearrangement of gears 730-2 and 730-1 may be necessary in order to provide a clearance space for inner tube 130 and gear 730-1. According to FIG. 7, axes LA, $SA_1$ and $SA_2$ are parallel to each other, as described in detail with respect to FIG. 2 above.

According to embodiments consistent with FIG. 7, while shaft 212-1 may rotate in a given direction, the rotation provided to tube 140 may be in the opposite direction. The same may be true for shaft 212-2 and tube 130. The end result is that tubes 130 and 140 have a counter-rotating motion relative to each other. Furthermore, the speed of each of tubes 130 and 140 may be adjusted independently of each other using actuators 721-1 and 721-2. Operation of engine 125 as illustrated in FIG. 7 uses the same pneumatic force to drive two counter-rotating motions.

FIG. 8A shows a portion of hand-piece 150 including motor portion 125, and cannula assembly 110, according to some embodiments. According to embodiments consistent with FIG. 8A, two separate flow channels 803-1 and 803-2 are provided, having a flow inlet 801-1 and 801-2, and an exhaust channel 802-1 and 802-2, respectively. For each flow channel, a drive fan 810-1 and 810-2 is placed tangential to the flow direction. Fans 810-1 and 810-2 are oriented in a plane including flow channels 803-1 and 803-2. Thus, the rotation axes of fans 810-1 and 810-2 are perpendicular to the direction of flow channels 803-1 and 803-2. Fans 810-1 and 810-2 include blades having a surface portion on a plane parallel to a plane including the fan axis. Furthermore, fans 810-1 and 810-2 may be placed so that flow channels 803-1 and 803-2 are interrupted along a small portion by the tip of the blades in the fans. As the fluid in channels 803-1 and 803-2 impinges on the blades of fans 810-1 and 810-2, momentum transfer from the fluid to the blades results in a rotational motion of the fans about their axes. Assembly 110 in FIG. 8A is consistent with the description of assembly 110 in FIG. 2 and in FIG. 3A above. Also, fiber routing path 470 running along LA is consistent with the description provided in relation to FIG. 6, above. Seal 215 in FIG. 8A is as described above in relation to FIG. 2.

According to embodiments consistent with FIG. 8A, transmission of the rotational motion form motor 125 to inner tube 130 and outer tube 140 may be provided directly through fans 810-2 and 810-1, respectively. Thus, in a configuration such as illustrated in FIG. 8A, less longitudinal space in hand-piece 150 is used; and fewer or no transmission gears are needed. In embodiments consistent with FIG. 8A, axes LA, $SA_1$ and $SA_2$ are collinear. On the other hand, the use of two flow channels 803-1 and 803-2 may be necessary, including inlet channels 801-1 and 801-2, and exhaust channels 802-1 and 802-2. As illustrated in FIG. 8A, the flow through channels 803-1 and 803-2 takes place in opposite directions. This provides opposing rotating motion to inner tube 130 (Fan 810-2) relative to outer tube 140 (Fan 810-1). Other configurations consistent with the concept illustrated in FIG. 8A may be possible, as will be described in detail in relation to FIG. 8B, below.

FIG. 8B shows a top-down view of a portion of motor 125 as in FIG. 8A, according to some embodiments. In the two configurations shown, 851 and 852, fans 810-1 and 810-2 are depicted separately, for clarity. It is understood that fans 810-1 and 810-2 are placed on top of each other, sharing their axis of rotation as illustrated in FIG. 8A above. In configuration 851, a counter-rotating motion is provided to fans 810-1 and 810-2 by placing flow channels 803-1 and 803-2 tangentially relative to the fans, and on opposite sides relative to the fan centers. In such configuration, having the fluid flow in the same direction in channels 803-1 and 803-2 results in a counter-rotating motion of fans 810-1 and 810-2. In configuration 852, a counter-rotating motion is provided to fans 810-1 and 810-2 by placing flow channels 803-1 and 803-2 tangentially relative to the fans and on the same side relative to the fan centers. In such configuration, having the fluid flow in opposite direction in channels 803-1 and 803-2 results in a counter-rotating motion of fans 810-1 and 810-2.

Note that a configuration such as 851 in FIG. 8B may allow motor 125 to have a single flow inlet 801 and a single exhaust 802 for both flow channels 803-1 and 803-2. Embodiments consistent with configuration 852 in FIG. 8B may have the advantage of reducing the cross-sectional space used in hand-piece 150 by only using one side of the fans 810-1 and 810-2 for a flow channel.

FIG. 9 shows a portion of hand-piece 150 including motor portion 125, transmission system 127, and cannula assembly 110 according to some embodiments. Embodiments consistent with FIG. 9 are analogous to embodiments as described in FIG. 7 in that two motors, 910-1 and 910-2 provide a counter-rotating motion to inner tube 130 and outer tube 140. Thus, transmission system 127 in FIG. 9 is as described in relation to FIG. 7 including the relative orientations of axes LA, $SA_1$ and $SA_2$. Assembly 110 in FIG. 9 is consistent with the description of assembly 110 in FIG. 2 and in FIG. 3A above. Also, fiber routing path 470 running along the axis of hand-piece 150 is consistent with the description provided in relation to FIG. 6, above.

Motors 910-1 and 910-2 in FIG. 9 may be electric motors, according to some embodiments. Thus, no fluid flow may be necessary in embodiments consistent with FIG. 9, and seal 215 may not be included in the design.

Figure 10:
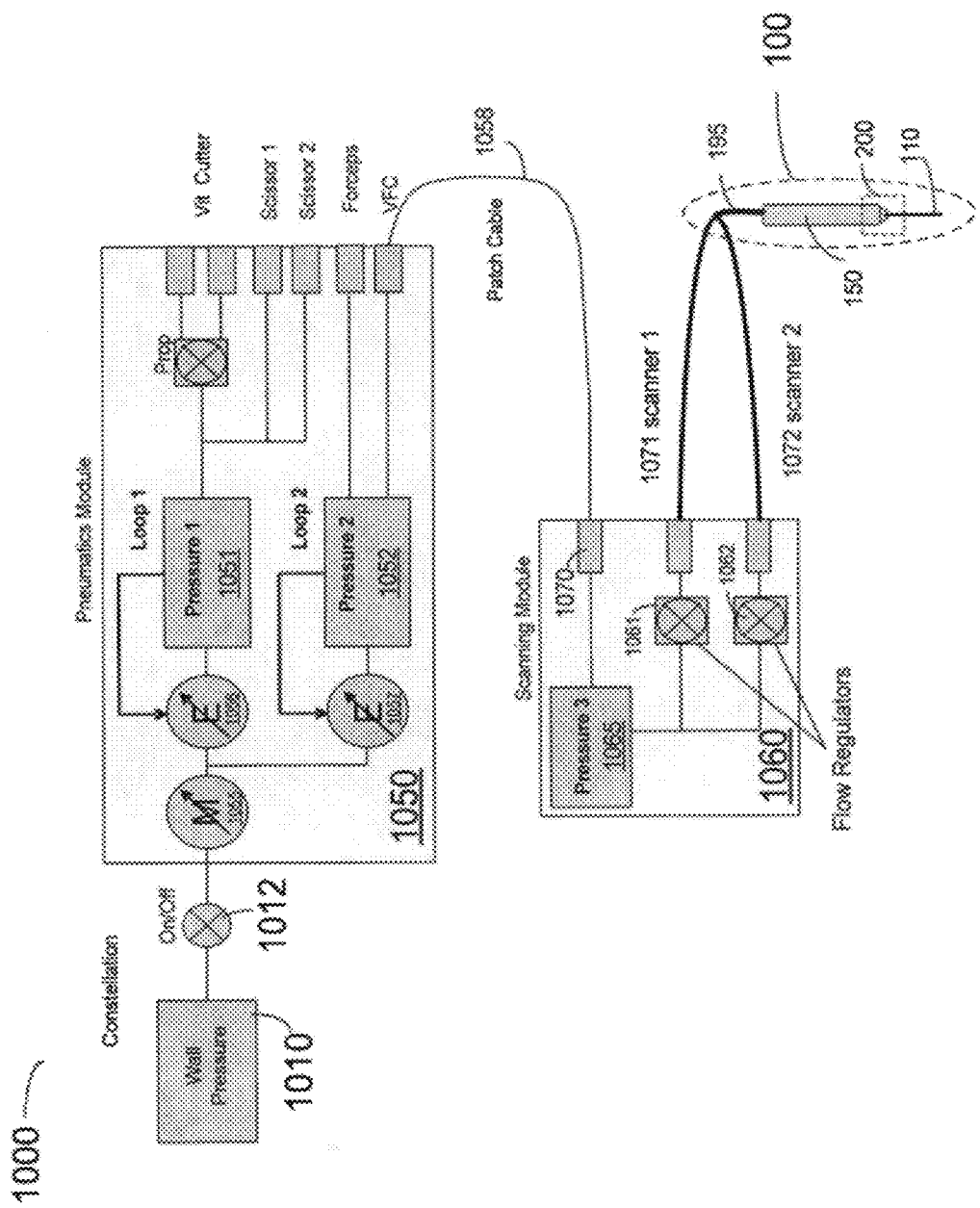
FIG. 10 shows a fluid console including a pneumatics module and a scanning module, according to some embodiments.

FIG. 10 shows fluid console 1000 including pneumatics module 1050, scanning module 1060, and endoprobe 100, according to some embodiments. According to FIG. 10, a pneumatic force is obtained from an external source such as a wall pressure connector 1010, engaged by 'On/Off' switch 1012. The pneumatic force is adjusted by module 1050 including elements 1055-1057. Mechanical regulator (M) 1055 is used to regulate incoming wall pressure approximately within the input range for electronic regulators (E) 1056 and (E) 1057. Electronic regulators (E) 1056 and (E) 1057 provide fine and controllable pressure regulation for pressure chambers 1051 and 1052. Regulators 1056 and 1057 are included in their respective control loops to control pressure in the corresponding chambers.

Pressure chamber 1051 provides a fluid with a first pressure (pressure 1), and pressure chamber 1052 provides a fluid with a second pressure (pressure 2). Pressure 1 may be used for a surgical operation different from that of pressure 2. For example in some embodiments pressure 1 may be used to operate a scissor system, or other mechanical element used during surgery. Further, the system may energize a cutter for vitrectomy procedures.

Pressure 2 provided by element 1052 is coupled to scanning module 1060 through patch cable 1058. Cable 1055 may be a plastic tubing able to contain a fluid at a pre-selected pressure. Scanning module 1060 may include inlet connector 1070 to receive cable 1055 and couple pressure 2 into element 1065. Element 1065 in turn converts pressure 2 into a pre-selected scanning pressure (pressure 3), which is coupled through valves 1061 and 1062 into flow channels 1071 for scanner 1, and 1072 for scanner 2. In some embodiments consistent with the description provided heretofore scanner 1 may include some of the elements in FIGS. 1-8 associated with the rotation of inner tube 130. Likewise, scanner 2 may include some of the elements in FIGS. 1-8 associated with the rotation of outer tube 140.

Scanning module 1060 may be an OCT scanning module according to some embodiments. In such cases, scanner 1 may be associated to inner tube 130 in assembly 110, having an optical element in the distal end. Likewise, scanner 2 may be associated to outer tube 140 in assembly 110, having an optical element in the distal end.

Probe 100 according to some embodiments disclosed herein may provide a simple, efficient system to generate precisely controlled counter rotational motion in two concentric tubes. Such an endoprobe may be used as an OCT imaging endoprobe, or a multi-spot laser endoprobe. While endoprobes may have 3-dimensional layouts, they may be highly constrained in cross-section, and elongated in a certain direction. Thus, a endoprobe according to embodiments described herein may have a longitudinal axis, which is the direction of the length of the endoprobe, and a cross section. Furthermore, in some embodiments the endoprobes may be axially symmetric, at least in a portion of the endoprobe which may include the distal end.

In OCT imaging techniques, a light beam having a coherence length may be directed to a certain spot in the target tissue by using an endoprobe. The coherence length provides a resolution depth, which when varied at the proximal end of the endoprobe may be de-convolved to produce an in-depth image of the illuminated portion of the tissue. An in-depth profile is normally referred to as an A-scan in OCT techniques. By scanning the illuminating spot along a line, an A-scan profile may be turned into a 2-dimensional tissue image. This may be referred to as a B-scan procedure in OCT techniques. In some embodiments, B-scans are straight lines along a cross-section of the tissue. Furthermore, by performing repeated B-scans along different lines in the tissue, a 3D rendition of the tissue may be provided. In some embodiments, the B-scans may be a set of lines having the same length and arranged in a radius from a common crossing point. Thus, a plurality of B-scans may provide an image of a circular area in the tissue, having a depth.

According to some embodiments of OCT scanning module 1060 a plurality of A-scans may be completed for each B-scan step. For example, 512 A-scans may be used to complete one B-scan. Some embodiments may use a lower number of A-scans per B-scan cycle, thus allowing the B-scan procedure to take place at a faster rate. In such cases, the rotating and counter-rotating speeds of tubes 130 and 140 may be further increased.

To obtain a complex set of scan lines, including B-scan lines arranged in pre-selected patterns, movable parts may be used at the distal end of the endoprobe. The movable parts may include delicate optical components moved to steer a light beam along a desired direction. Precise control of this motion is important for the efficacy of OCT procedures. In particular, repeatability of the motion may be required so that A-scans may be aligned along B-scan lines to conform a continuous image. In some embodiments, the motion of movable parts in the endoprobe may be a periodic cycle having a closed trajectory. For example, a trajectory may be circular, centered on the endoprobe axis. The endoprobe longitudinal axis may be the optical axis of an optical system.

A substantially one dimensional endoprobe having a symmetry axis according to some embodiments disclosed herein may provide radially oriented B-scans about the endoprobe axis. To achieve this, two counter-rotating elements may be used, synchronized accordingly by a transmission system using a combination of gears. For example, two counter rotating elements arranged concentrically about the endoprobe axis may provide optical scanning of a beam along a radial direction in a plane perpendicular to and centered on the endoprobe axis. Such an arrangement may use optical elements as described in detail in the paper by Wu et al. incorporated herein by reference in its entirety (J. Wu, M. Conry, C. Gu, F. Wang, Z. Yaqoob, and C. Yang; "Paired-angle-rotation scanning optical coherence tomography forward-imaging endoprobe" Optics Letters, 31(9) 1265 (2006)). Some embodiments may include a synchronization system such that the relative phase and speed of the two counter-rotating elements may be regulated as desired. Thus, two counter rotating elements may provide linear radial scanning along a plane including the endoprobe axis. Furthermore, by adjusting the relative angular speeds and phases of the counter rotating elements, the plane of the radial scan may be rotated about the endoprobe axis. Some embodiments as described above may be such that the radial scan is not perfectly linear. That is, the optical beam may not move in a perfect line contained within a plane including the endoprobe axis. In some embodiments the motion may be substantially close to the plane, on an elongated trajectory substantially close to a line in the plane. In some embodiments, the trajectory of the optical beam may form an elongated '8' figure on a plane perpendicular to and centered on the endoprobe axis.

In some embodiments, OCT techniques use forward-directed scan procedures. In this case, optical illumination takes place in the forward direction of the endoprobe axis. In forward-directed scans, the target tissue may be ahead of the endoprobe in a plane perpendicular to the endoprobe axis. Thus, light traveling from the tip of the endoprobe to the tissue, and back from the tissue into the endoprobe may travel in a direction substantially parallel to the endoprobe axis. In some embodiments using forward-directed scans, the target tissue may be approximately perpendicular to the endoprobe axis, but not exactly. Furthermore, in some embodiments light traveling to and from the target tissue from and into the endoprobe may not be parallel to the endoprobe axis, but form a symmetric pattern about the endoprobe axis. For example, light illuminating the target tissue in a forward-directed scan may form a solid cone or a portion thereof about the endoprobe axis. Likewise, light collected by the endoprobe in a forward-directed scan may come from target tissue in a 3D region including a portion of a cone section around the endoprobe axis.

In some embodiments, an OCT technique may use side imaging. For example, in side imaging the target tissue may be parallel to a plane containing the endoprobe axis. In a situation like this, it may be desirable to move the illumination spot in a circular trajectory around the endoprobe axis, to create a closed-loop image of the target tissue. Such a situation may arise in ophthalmic microsurgery involving endovascular procedures. For example, in coronary angiography the interior wall of the coronary artery may be fully scanned in cylindrical sections along the arterial lumen using embodiments described herein.

Some embodiments may use endoprobes as provided herein for delivery of laser light intended for therapeutic purposes. For example, in photodynamic procedures a laser light may be scanned to activate a chemical agent present in a drug previously delivered to the target tissue. In some embodiments, laser light may be used to selectively oblate or remove tissue or residual materials from the target areas. In embodiments such as previously described, precise control of the light being delivered is provided by movable components in the distal end of the endoprobe.

Note that the conversion of rotational motion into linear motion according to some embodiments disclosed herein provides a smooth system to perform a linear motion. While rotational motion may be provided continuously, a cyclic linear motion may require stoppage and acceleration of a mechanical element, if tried directly. Stoppage and acceleration of a mechanical element subject to friction may not be desirable.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:
1. An ophthalmic endoprobe comprising:
a hand-piece coupled to a cannula assembly having a longitudinal axis, the cannula assembly comprising an inner tube concentric with an outer tube; wherein the hand-piece further comprises
a motor comprising a mechanical piston moved in a longitudinal direction by a pressurized fluid, the mechanical piston providing motion to a transmission shaft; and
a transmission system to couple the shaft motion to the cannula assembly, the transmission system configured to counter-rotate the inner tube and the outer tube about the longitudinal axis of the cannula assembly, the transmission system comprising an uncoupled gear system for independent rotation of the inner tube and the outer tube.

2. The ophthalmic endoprobe of claim 1 wherein the transmission system comprises an oscillating gear allowed to rotate along the piston shaft in one direction only about the axis of the cannula tubes.

3. The ophthalmic endoprobe of claim 1 wherein the transmission system comprises a worm gear.

4. The ophthalmic endoprobe of claim 1 wherein the transmission system comprises a spline gear.

5. The ophthalmic endoprobe of claim 1 wherein the transmission system comprises a one-way bearing.

6. The ophthalmic endoprobe of claim 1 wherein the motor comprises at least two mechanical pistons each moved in the longitudinal direction by the pressurized fluid.

7. The ophthalmic endoprobe of claim 6 wherein the transmission system couples the motion of the at least two mechanical pistons into rotational motion of a shaft using a crankshaft.

8. The ophthalmic endoprobe of claim 7 wherein the crankshaft is perpendicular to the longitudinal axis in the cannula assembly.

9. The ophthalmic endoprobe of claim 8 wherein the transmission system comprises at least two conical gears perpendicular to each other to couple the crankshaft motion to the inner tube and the outer tube in the cannula assembly.

10. The ophthalmic endoprobe of claim 1 further comprising a stationary outer cannula adapted to provide a protective cover to the cannula assembly comprising the inner tube concentric with the outer tube.

* * * * *